(12) United States Patent
Beroza

(10) Patent No.: US 7,712,248 B2
(45) Date of Patent: May 11, 2010

(54) INSECT ATTRACTANT RELEASING DEVICE

(75) Inventor: Morton Beroza, Silver Spring, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 1131 days.

(21) Appl. No.: 10/803,121

(22) Filed: Mar. 17, 2004

(65) Prior Publication Data
US 2004/0216369 A1   Nov. 4, 2004

Related U.S. Application Data

(63) Continuation-in-part of application No. 10/247,739, filed on Sep. 20, 2002.

(51) Int. Cl.
*A01M 1/02* (2006.01)
*A01M 1/20* (2006.01)
(52) U.S. Cl. .............. 43/131; 43/107; 43/122; 43/132.1
(58) Field of Classification Search ............ 43/107, 43/122, 123, 124, 131, 132.1
See application file for complete search history.

(56) References Cited

U.S. PATENT DOCUMENTS

| 1,056,535 | A | * | 3/1913 | Grimes et al. ............ 43/131 |
|---|---|---|---|---|
| 1,924,379 | A | | 8/1933 | Reese |
| 2,176,345 | A | * | 10/1939 | Hurwitt .................. 43/131 |
| 2,254,948 | A | * | 9/1941 | Kubalek .................. 43/131 |
| 2,573,672 | A | | 10/1951 | Reinhardt |
| 4,662,103 | A | | 5/1987 | Cheng |
| 4,745,705 | A | | 5/1988 | Yamamoto et al. |
| 4,802,303 | A | | 2/1989 | Floyd, III |
| 4,908,977 | A | | 3/1990 | Foster |
| 5,018,299 | A | | 5/1991 | Peek et al. |
| 5,501,033 | A | | 3/1996 | Wefler |
| 5,588,255 | A | | 12/1996 | Johnson |
| 5,647,164 | A | | 7/1997 | Yates |
| 5,749,168 | A | * | 5/1998 | Chrysanthis ............ 43/122 |
| 5,906,298 | A | | 5/1999 | Ward |
| 6,209,252 | B1 | | 4/2001 | McGough |
| 6,223,465 | B1 | | 5/2001 | Soller et al. |
| 6,482,365 | B1 | | 11/2002 | Soller |
| 6,530,172 | B2 | | 3/2003 | Lenz |
| 6,532,695 | B1 | | 3/2003 | Alvarado |
| 6,543,181 | B1 | * | 4/2003 | Baker et al. ............ 43/107 |
| 6,553,712 | B1 | * | 4/2003 | Majerowski et al. ...... 43/131 |
| RE38,150 | E | | 6/2003 | Greatbatch et al. |
| 6,585,990 | B1 | * | 7/2003 | Huang .................. 424/405 |
| 6,631,891 | B1 | | 10/2003 | Slade |
| 6,648,239 | B1 | | 11/2003 | Myny et al. |
| 2003/0061757 | A1 | | 4/2003 | Askin |
| 2004/0055207 | A1 | | 3/2004 | Beroza |

FOREIGN PATENT DOCUMENTS

| EP | 0420144 | * | 4/1991 |
|---|---|---|---|
| JP | 4179426 | | 6/1992 |
| JP | 4-200336 | * | 7/1992 |

* cited by examiner

*Primary Examiner*—David J Parsley
(74) *Attorney, Agent, or Firm*—John D. Fado; Gail E. Poulos

(57) ABSTRACT

A device for uniform emission of a composition having at least one volatile liquid attractant. It is especially useful in traps to improve the monitoring of pest insect populations and/or for mass trapping of insects.

6 Claims, 10 Drawing Sheets

INSECT ATTRACTANT RELEASING DEVICE

This application is a Continuation-In-Part application of pending U.S. patent application Ser. No. 10/247,739, filed on Sep. 9, 2002.

This invention was sponsored by the United States Department of Agriculture Agreement Number 58-0790-2-154.

BACKGROUND OF THE INVENTION

1. Field of the Invention

The present invention relates to a device for use in traps for monitoring and/or capturing pest flying insects. The device permits uniform, extended emissions of an insect attractant in amounts that are attractive to the targeted flying insect.

2. Description of the Related Art

Insect lures (attractants) are currently employed to detect and monitor for the presence of insects that respond to lure-baited traps, such as for example, the Mediterranean fruit fly (medfly), melon fly, codling moth, mosquito, etc. Lures emitted from insect traps travel downwind for great distances which allow monitoring traps to be placed as much as a mile apart. Responding insects, on detecting the lure scent, fly upwind until they locate the trap, enter it, and are caught. If the responding insect loses the scent, it will circle back and forth cross-wind until it again locates the scent and then continue to move toward the lure in the trap. Insects are extremely sensitive to lures especially sex lures which help insects find the opposite sex for mating and propagation. Male gypsy moths, for example, have been found to respond to 1 ng of suitably formulated DISPARLURE (gypsy moth pheromone) in traps for 3 months in the field (Beroza et al., J. Econ. Entomol., Vol. 64, 1499-1508, 1971). Insects will not enter a trap if lure emission is too high and they will have difficulty finding the trap if lure emission is too low. For maximum efficiency with a given trap, the lure level must be as high as possible in order to draw the targeted insects from as far away as possible but not so high as to repel or prevent the responding insect from entering the trap. The information derived from the lure-baited traps is used to determine where and when control measures are needed, such action being more environmentally friendly and cost effective than widespread application of insecticides used in the past. Such control measures can include insecticide application, sterile-insect release, mass trapping, etc. For medflies, traps are manually examined every two to three weeks to see if any insects are in the traps and to rebait the traps. Targeted pests, such as for example, the Mediterranean fruit fly (Medflies), cause damage to fruits and vegetables during the course of a season that has been estimated to amount to millions of dollars. In order to effect control of these targeted pest insects, it is necessary to locate the area and determine the degree of infestation. This may be done by setting out traps in suspected areas and placing in the traps a bait and/or attractant for the targeted pest. In the case of Mediterranean fruit flies, approximately 150,000 traps containing the attractant TRIMEDLURE are deployed in California. If Medflies should come into the United States and are trapped, thousands more traps will be deployed in a mass trapping effort to confine the flies in one area where they can be destroyed. Over one million TRIMEDLURE plugs are sold in the United States each year to keep the traps effective.

Wick-based, liquid emanation systems are known. Typically, in such systems, one end of a wick is partially submerged in a liquid to be dispensed. The liquid is contained in any suitable container. The partially submerged portion of the wick absorbs the liquid, some of which diffuses by capillary or wicking action into the exposed portion of the wick. In prior art systems, the exposed portion of the wick is heated, often by means of a ring-shaped heater which fits over the wick.

In other systems, a liquid containing a scent or pheromone is poured onto an absorbent material such as a wick. The wick is then placed in a trap and there is no way to control the amount of scent or pheromone being released thus resulting in expensive waste. Furthermore, emission rates decline rapidly over time. For example, TRIMEDLURE, a Mediterranean fruit fly lure, is absorbed on a cotton plug that emits TRIMEDLURE at an ever-declining rate resulting in the plug replacement every 2-3 weeks.

There remains a need in the art for an effective flying insect attractant emission device which delivers flying insect attracting amounts of an attractant at constant emission rates, i.e., at the lure=s most attractive level, over extended periods of time. The present invention provides a device that improves the trapping efficiency of insect traps by providing a constant emission rate of insect attracting amounts of a composition containing at least one flying insect attractant over periods of time greater than that achieved by prior art devices and is different than prior art devices used for insect lures.

SUMMARY OF THE INVENTION

It is therefore an object of the present invention to provide an effective flying insect attractant device that delivers insect attracting-emitting amounts of a composition having at least one volatile liquid attractant at a constant rate over extended periods of time.

A further object of the present invention is to provide a device containing a composition having at least one volatile liquid attractant wherein said device includes an adjustable wick for providing maximum insect attraction.

A still further object of the present invention is to provide a device containing a composition having at least one volatile liquid attractant for flying insects wherein said composition further includes at least one volatile insecticide. Further objects and advantages of the invention will become apparent from the following description

DETAILED DESCRIPTION OF THE INVENTION

Figure 1:
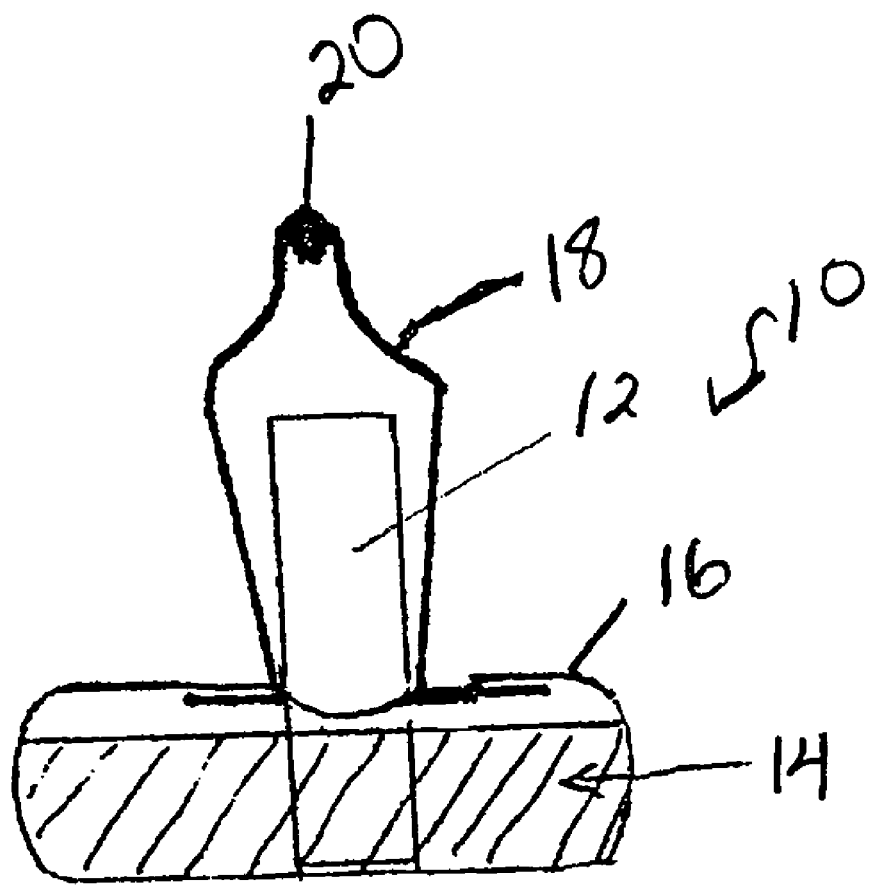
FIG. 1 is a side-view drawing showing one embodiment of device 10 with wick 12, liquid lure 14, container 16, hanging means 18, and anchor 20.
Figure 2:
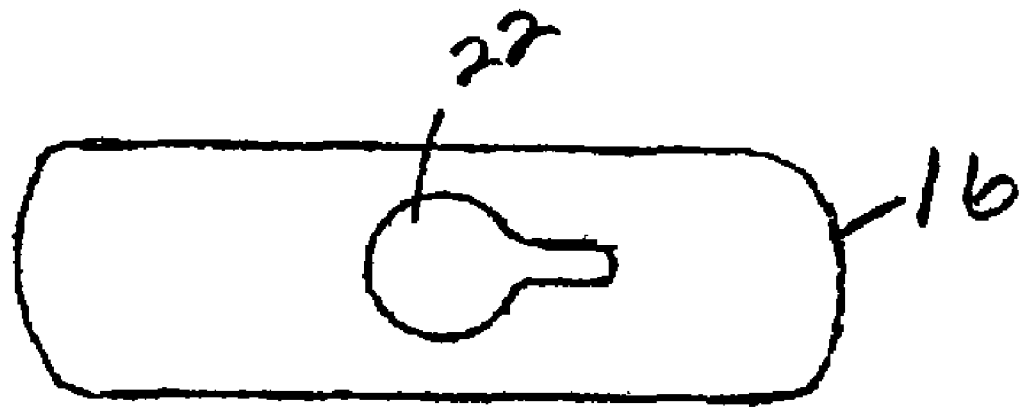
FIG. 2 is a top-view drawing of container 16 showing key-shaped-opening 22.
Figure 3:
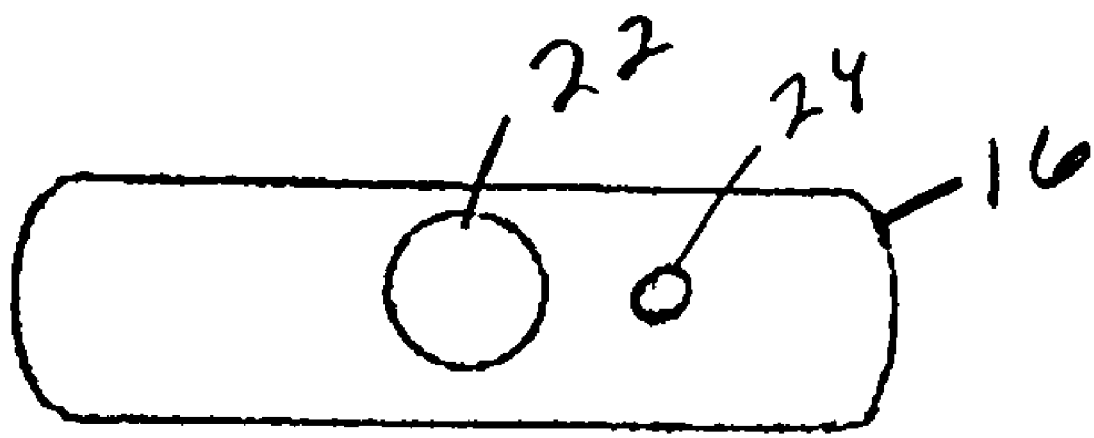
FIG. 3 is a drawing of another embodiment of device 10 showing container 16, wick opening 22 and vent opening 24.

The present invention provides a flying insect attractant-emitting device 10 which provides uniform emission of a volatile liquid attractant 14 over extended periods of time and is depicted in FIGS. 1-3. Device 10 includes a container 16, wick 12, wick opening 22, optionally hanging means 18 and optionally anchor 20. Container 16 can be made of any inert material such as glass, plastic, etc. Container 16 is of a size to hold an amount of volatile liquid attractant 14 needed for a desired period of time. Wick opening 22 on top of container 16 should be only large enough to frictionally insert and frictionally support wick 12 and can be of any shape. In one embodiment, wick opening 22 is key-shaped to allow air to enter the container through the elongated portion of opening 22 as the attractant is absorbed by wick 12 enabling air pressure to allow a steady flow of attractant up the wick (FIG. 2). Wick opening 22 can be of any shape as long as the wick is frictionally supported and there is a portion of the opening that will allow air to flow into container 16. Furthermore, liquid attractant 14 can be replenished through the elongated portion of wick opening 22. The elongated portion is narrower than wick opening 22 but large enough to prevent film closure if attractant 14 should splash up on the inside of the top of container 16 such as could happen in a wind storm, refilling device 10, or if jiggled by a passing animal, or when the trap containing device 10 is examined for insect capture. In a second embodiment of the present invention, container 16 has wick opening 22 that is large enough to frictionally insert and frictionally support wick 12. It is shown in FIG. 3 as circular in shape but can be of any shape to accommodate the shape and size of wick 12. Container 16 also has vent opening 24 which can be of any shape to allow air to enter container 16 and is smaller relative to wick opening 22 but large enough to prevent film closure if attractant 14 should splash up on the inside of the top of container 16 such as could happen in a wind storm, refilling of device 10, or if jiggled by a passing animal or when the trap is examined for insect capture. As in the first embodiment, attractant 14 can be replenished through vent opening 24.

Wick 12 is a standard wick known in the art. Wick 12 can be made of any absorbent inert material and be of any shape. Opening 22 is sized to fit any size and shape wick 12. The outer end of wick 12 extends above the top of container 16 and the inner end sits in liquid attractant 14 and is placed close to the bottom of container 16 and can even rest on the bottom of container 16. It should be positioned so that it will always be in contact with liquid attractant 14 regardless of the volume of attractant 14 remaining in container 16. The outer end of wick 12 is extended to a length which gives maximum insect attraction and capture. For TRIMEDLURE, for example, the outer portion of wick 12 should be from about ¼ inch to about ¾ inch from the top of container 16, with about 2 inch preferred. One of ordinary skill in the art could readily determine wick length for other attractants given the teachings of the present detailed description. The total length of the wick is determined by the depth of container 16, and the amount of exposed wick for a particular attractant.

Attractant 14 refers to any liquid chemical composition that includes an individual compound or a composition including more than one compound that either directly or indirectly, such as into the wind, causes the insect to displace toward the attractant 14. Examples of useful attractants 14 in the present invention include, for example, TRIMEDLURE CUELURE, MUSCALURE, etc. An inert liquid, with a volatility similar to attractant 14, can optionally be added to attractant 14 to reduce the rate of attractant evaporation when needed. If attractant 14 is a solid at room temperatures, it can be dissolved in a liquid carrier to allow its use in device 10. More than one attractant 14 can be used in a trap by either combining different attractants 14 in the same device 10 or by placing more than one device 10, each containing a different attractant 14, in a trap. It is important in either case that the different attractants 14 do not appreciably interfere with each other=s attracting ability. Device 10 is used in any trap used to capture and/or kill insects. Device 10 can be placed in a trap by either sitting it on a flat surface of the trap, hanging it using a wire hanger 18 and anchor 20 as depicted in FIG. 1, affixing to the trap using any means for affixing such as for example an adhesive, VELCRO, fasteners, etc. Any means for placing device 10 in a trap is well within the ordinary skill in art given the present description of the invention. Although it may be desirable to replace wick 12, device 10 can be used indefinitely and repeatedly since it does not deteriorate.

In operation, device 10 is placed in a trapping device that is deployed in infested areas usually by hanging the trap containing device 10 in trees or shrubs. The traps are checked periodically for insects and attractant 14 levels. The level of attractant 14 is readily visible especially if an inert color is added to attractant 14. With the present invention, there is no need to replenish attractant 14 for at least several months, as will be shown in the examples below. Thus, when an infested area is located, many traps with device 10 can be deployed in the area to monitor, control, and/or eradicate the targeted insects. These traps having device 10 can also be used in areas to capture insects as soon as they achieve flying status.

The following examples illustrate the use of the invention. They are intended to further illustrate the invention and are not intended to limit the scope of the invention as defined by the claims. The attractant TRIMEDLURE and CUELURE are used as model attractants for device 10.

EXAMPLE 1

Figure 4:
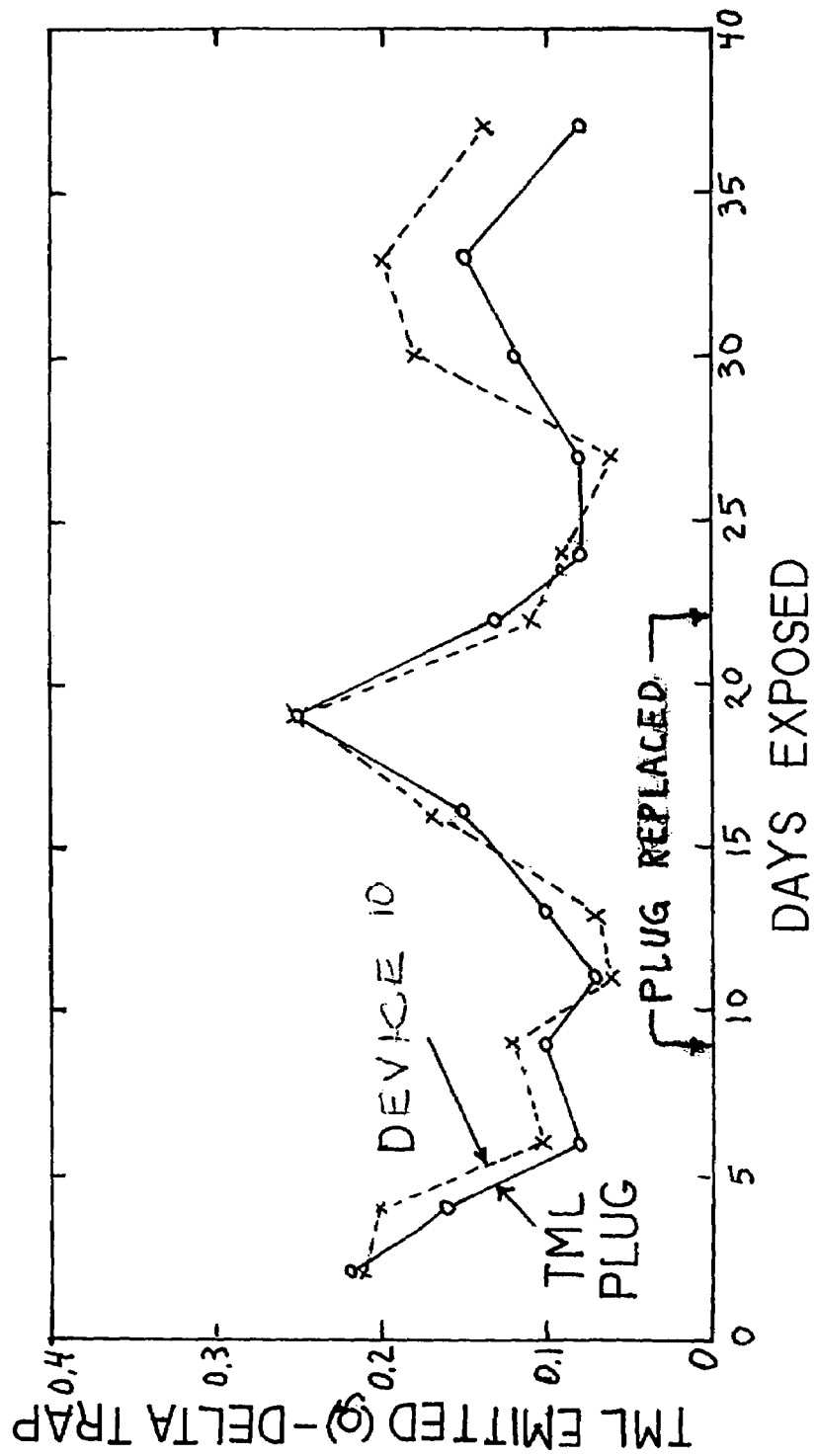
FIG. 4 is a graph showing TRIMEDLURE emission over a period of about 37 days using device 10 vs. TRIMEDLURE plug (Dow Corning) when placed outdoors during August-September.

Tests were conducted with TRIMEDLURE (TML) using device 10 shown in FIG. 1. TRIMEDLURE was placed in device 10, and device 10 was placed in a Delta trap. Another Delta trap contained the commercial lure, the Magnet TRI-MEDLURE 70-0 Plug (Dow Corning). Delta traps are coated with a sticky substance that traps insects responding to the attractant. The traps were placed outdoors during August-September in Silver Spring, Md. The loss of TRIMEDLURE from each attractant device was measured every few days by weighing the lure dispensers for 37 days. Results are shown in FIG. 4. Losses of TRIMEDLURE from device 10 and the TML plug were consistently the same during the 37-day outdoor test. Although loss of TRIMEDLURE depended on the temperature, losses of TRIMEDLURE from device 10 and the TML plug exposed under identical conditions were consistently very similar, the important difference being that the plug had to be replaced twice at about day 8 and day 22 while the liquid attractant in device 10 did not have to be refilled over the 37 day period.

EXAMPLE 2

Figure 5:
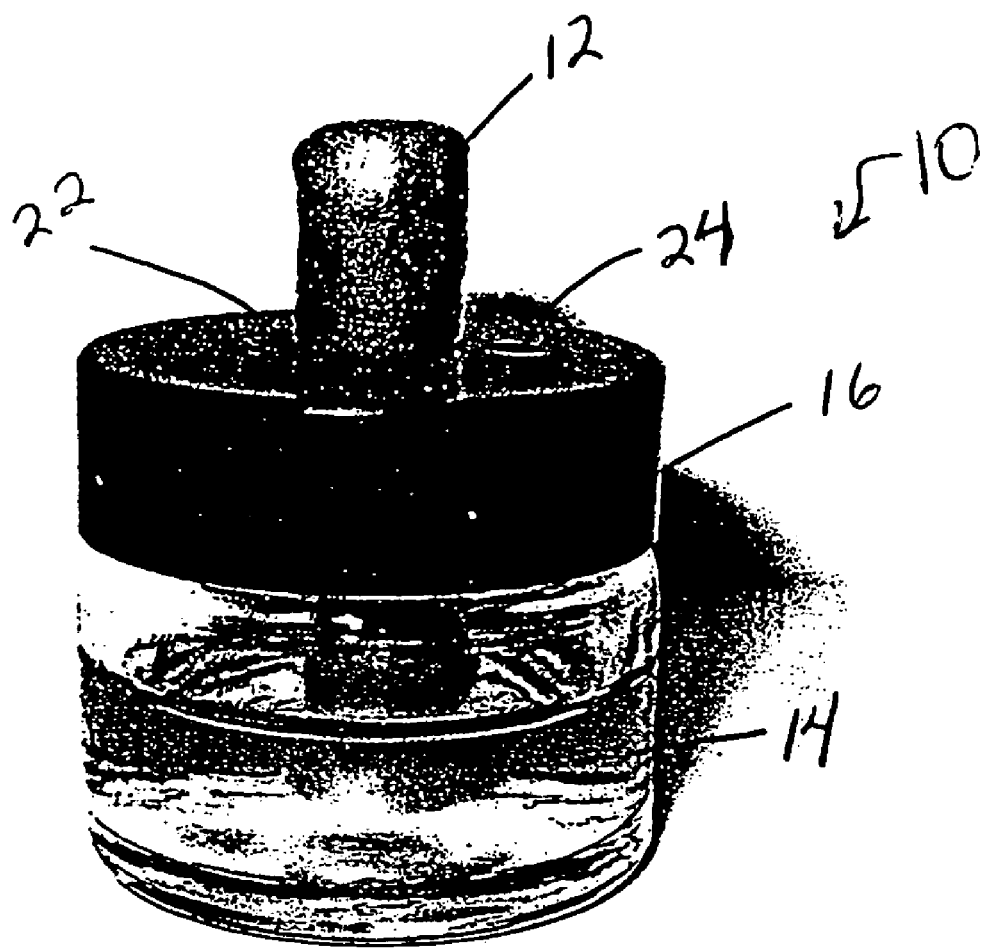
FIG. 5 is a photograph of another embodiment of the invention showing container 16, wick 12, attractant 14, wick opening 22, and vent opening 24.
Figure 6:
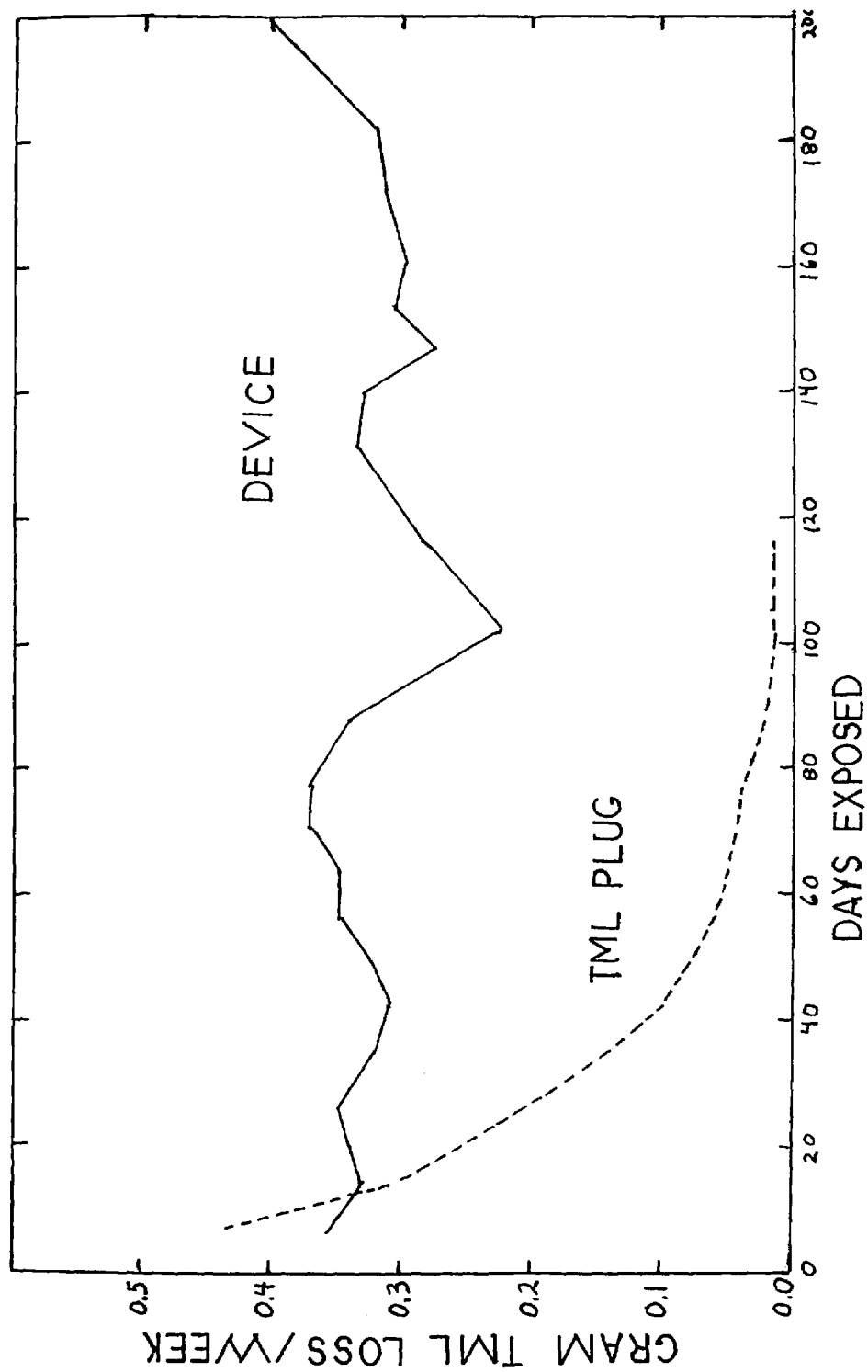
FIG. 6 is a graph showing TRIMEDLURE loss in grams/week over about 200 days when device 10 and a TRIMEDLURE plug were placed in a laboratory exhaust hood kept at about 25 degrees C.

TRIMEDLURE emission from device 10, as depicted in FIG. 5 and from the TML plug, as described above in Example 1, was measured by weight loss of device 10 and TML plug over 200 days as in Example 1. Device 10 and TML plug were placed in a laboratory hood at 25 degrees C. Results are shown in FIG. 6. FIG. 6 shows that device 10 provides a relatively constant evaporation rate over time, while the evaporation from the TML plug is not constant but declines rapidly with time. Also shown is that Device 10 provides constant lure emission over a period of at least 200 days. Thus, the major benefit of this invention is that device 10 can emit its attractant at its most attractive level, and at the same time, can emit at this level for about 6 months or more.

EXAMPLE 3

Figure 7:
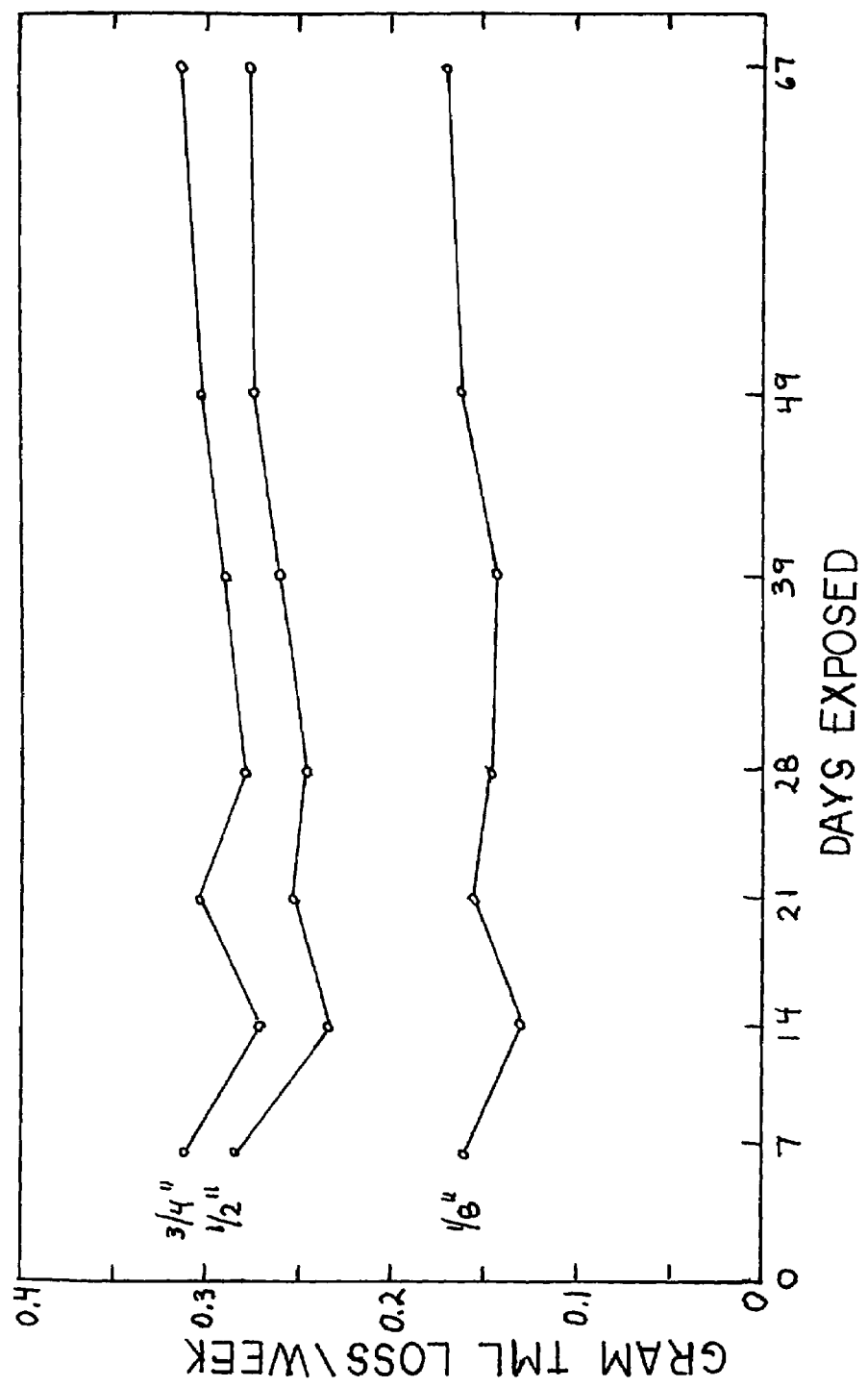
FIG. 7 is a graph showing TRIMEDLURE loss/week from device 10 with different lengths of exposed wick in a laboratory exhaust hood at 25 degrees C. over about 67 days.

This example demonstrates the regulation of attractant emission from device 10 by the amount of wick exposed to the atmosphere. TML loss was measured by loss of weight of device 10 over 67 days using exposed wick lengths of about ⅛ inch, about 2 inch, and about ¾ inch. Devices 10 were placed in a laboratory hood at 25 degrees C. for 67 days. Results are shown in FIG. 7. With each length, emission remained relatively constant over 67 days and wick length regulated attractant emission.

EXAMPLE 4

Field tests were conducted to determine which wick length provided the best attraction. In this example the tests were conducted in a coffee field in Kalaheo, Hawaii from August-November. Accordingly, Jackson traps with device 10 having exposed wick lengths of about ¼ inch, about 2 inch, and about ¾ inch, TML plugs, and controls (no attractant) were set out. Mean captures of medflies were obtained weekly over about a 10 week period (See Table 1 below). From Table 1, the about 2 inch exposed wick length is shown to be the most effective.

TABLE 1

Mean Capture of Medflies over 10 weeks

| Week | Control | TML ¼" | TML 2" | TML ¾" | TML Plug |
|---|---|---|---|---|---|
| 1 | 0 | 86.67 | 191.33 | 87.67 | 75.67 |
| 2 | 0 | 250.6 | 773.83 | 420.20 | 299.33 |
| 3 | 0 | 810.67 | 1004.33 | 822.67 | 762.67 |
| 4 | 0 | 888.67 | 1488.00 | 1274.67 | 1314.67 |
| 5 | 0 | 2316.67 | 2672.61 | 2293.33 | 1987.33 |
| 6 | 0 | 2818.67 | 4165.33 | 3610.67 | 2806.67 |
| 7 | 0 | 3916.67 | 4382.00 | 4212.33 | 3994.67 |
| 8 | nd* | nd* | nd* | nd* | nd |
| 9 | 0 | 2006.00 | 1847.20 | 1477.33 | 1882.67 |
| 10 | 0 | 2094.00 | 2616.00 | 2293.33 | 1700.00 |

*nd = no data due to storm

EXAMPLE 5

Figure 8:
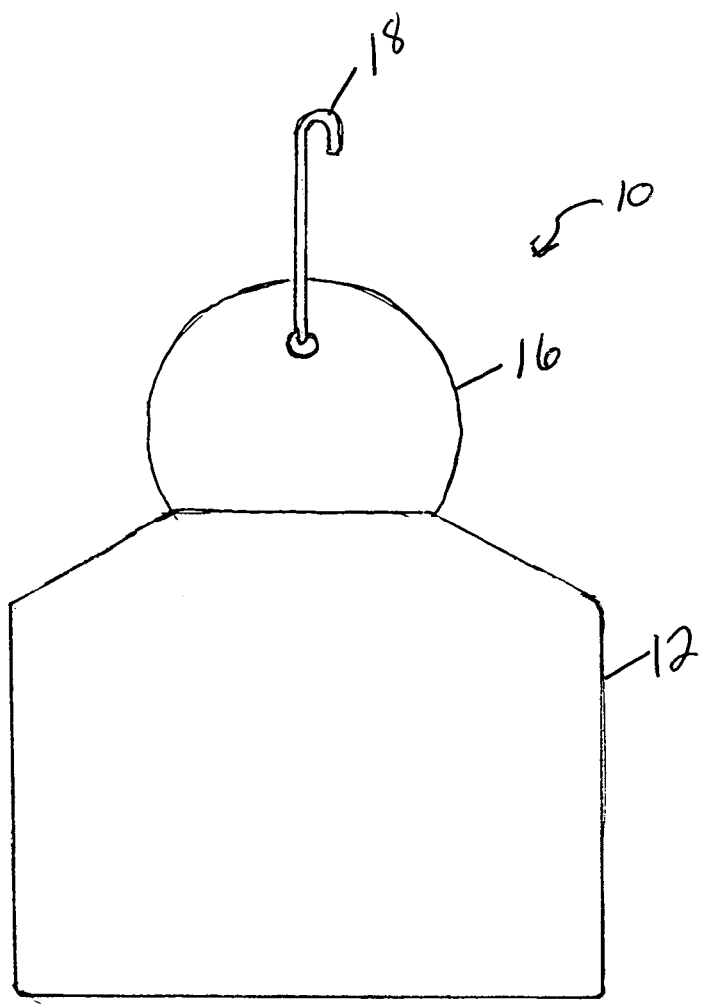
FIG. 8 is a front view drawing of another embodiment of device 10 showing blotter-like wick 12, container 16, and hanging means 18.
Figure 9:
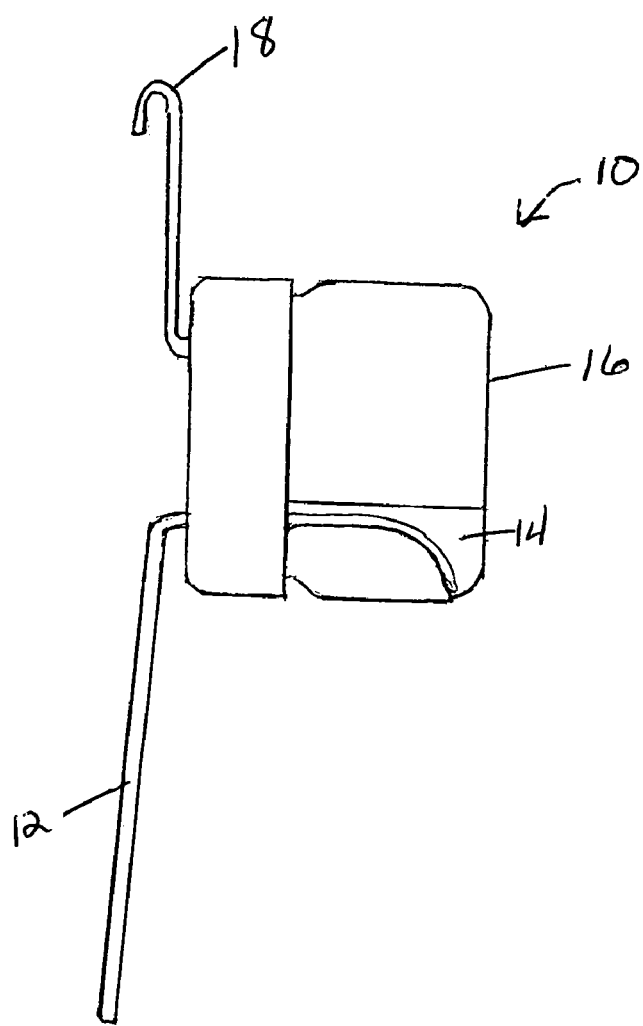
FIG. 9 is a side view drawing of device 10 shown in FIG. 8 showing blotter-like wick 12, container 16, attractant 14, and hanging means 18.

CUELURE was tested using an embodiment of the present invention that included a blotter-like wick in device 10 (FIGS. 8 and 9). Device 10 with CUELURE was placed in a lab hood at about 23-25 degrees C. for about 75 days to determine the emission rate by measuring weight loss as shown in Table 2 below. Excluding the first week to allow device 10 to equilibrate, CUELURE emission rate averaged about 30 mg/week±4 mg/week.

TABLE 2

CUELURE emission rate as determined by weight loss

| Temp °C. | Days | Assembly Weight (g) | Weight Loss (g) | Weight Loss (g)/week |
|---|---|---|---|---|
| 24.5 | 0 | 50.484 | — | — |
| 24.5 | 7 | 50.430 | 0.054 | 0.054 |
| 25.0 | 14 | 50.398 | 0.032 | 0.032 |
| 26.0 | 25 | 50.353 | 0.045 | 0.027 |
| 23.0 | 35 | 50.300 | 0.053 | 0.037 |
| 23.0 | 53 | 50.217 | 0.083 | 0.032 |
| 23.0 | 75 | 50.145 | 0.072 | 0.022 |

EXAMPLE 6

Figure 10:
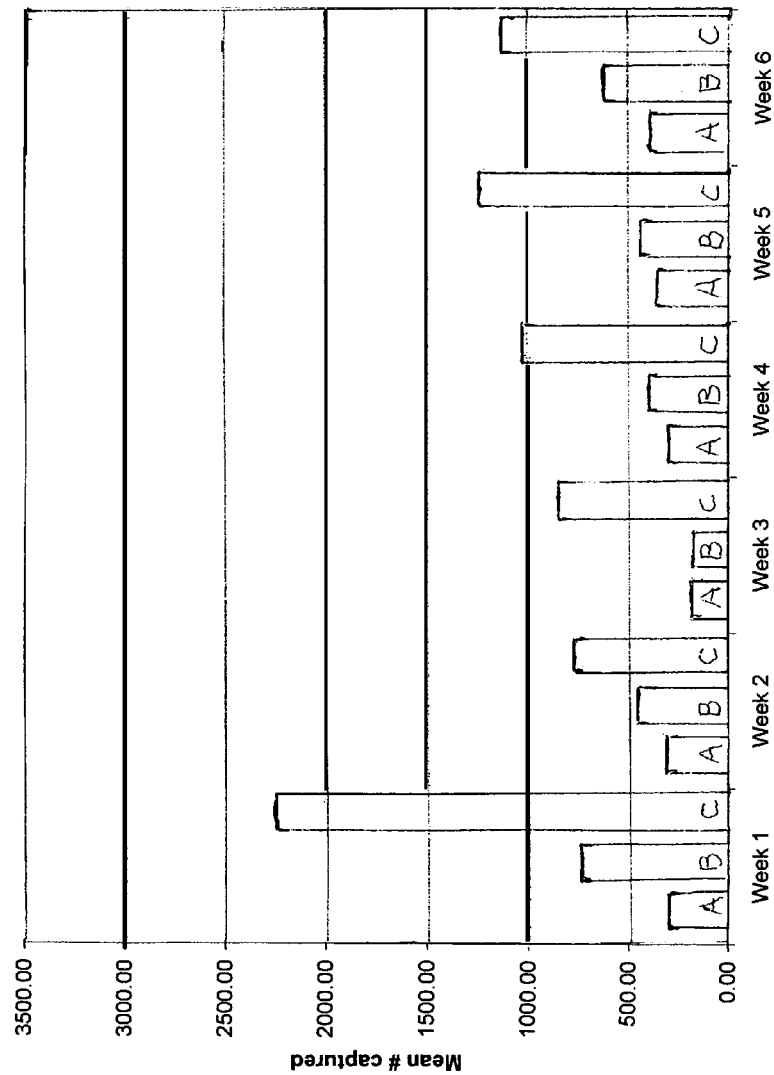
FIG. 10 is a graph showing wild melon flies response to CUELURE and Sentry plugs (containing CUELURE) over a three week period. A=CUELURE Plug, B=Sentry Plug, C=device 10.

Melon fly capture tests were conducted in papaya fields in Kapoho on the island of Hawaii. Traps were placed in the fields for a period of six weeks and included CUELURE and Sentry plugs (A and B, respectively in FIG. 10) and traps with device 10 (C in FIG. 10) as depicted in FIGS. 8 and 9. Device 10 contained liquid CUELURE. Traps were checked weekly for captured insects over a period of six weeks. Results are shown in FIG. 10. Catches in device 10 (C) exceeded those of the commercially available CUELURE dispensers (A and B) currently used.

The foregoing detailed description is for the purpose of illustration. Such detail is solely for that purpose and those skilled in the art can make variations without departing from the spirit and scope of the invention.

What is claimed is:

1. A device for providing uniform emission of a flying insect attractant consisting of:
    (a) a container having a top surface, a bottom surface, and side walls, having a composition of at least one volatile liquid attractant specific for one targeted flying insect species, and a first opening in the top of said container to receive a wick;
    (b) an adjustable wick frictionally inserted into said first opening of said container wherein a portion of said wick area is exposed externally to an atmosphere and said exposed wick area can be increased or decreased over time to maintain a uniform rate of emission providing maximum attraction for said flying insect, and
    (c) a second opening in the top of said container, smaller than said first opening and large enough to prevent film closure by a liquid,
wherein said second opening maintains air pressure in said container and wherein said container emits said at least one volatile attractant for at least about six months without replenishment of said attractant.

2. The device of claim 1 wherein said composition further includes at least one volatile insecticide wherein said at least one volatile insecticide is absorbed by said wick.

3. The device of claim 1 wherein said first and second opening form a single opening with the first opening being of a size to frictionally hold a wick and said second opening is elongated and narrower than said first opening.

4. A trap for flying insects comprising:
    (a) an open ended trap that allows air passage through said trap comprising a device consisting of a container having a top surface, a bottom surface, and side walls, having a composition of at least one volatile liquid attractant specific for one targeted flying insect species, and a first opening in the top of said container to frictionally receive a wick;

(b) an adjustable wick frictionally inserted into said first opening of said container wherein the length of said wick is frictionally adjustable to provide a uniform emission rate of said at least one attractant which results in maximum attraction of said flying insect over an extended period, and (c) a second opening in the top of said container, smaller than said first opening and large enough to prevent film closure by a liquid, wherein said second opening maintains air pressure in said container and wherein said container emits said at least one volatile attractant for at least about six months without replenishment of said attractant.

5. The trap of claim 4 wherein said composition further includes at least one volatile insecticide wherein said at least one volatile insecticide is absorbed by said wick.

6. A method for mass trapping of at least one targeted flying insect comprising:

(a) placing in an open ended trap that allows air passage through said trap, at least one device consisting of a container, having a top surface and bottom surface and side walls, having a composition of at least one volatile liquid attractant specific for one targeted flying insect species and a first opening to frictionally receive a wick, a wick inserted into said first opening of said container wherein the length of said wick is frictionally adjustable to provide a uniform emission rate of said at least one volatile attractant which results in maximum attraction of said one targeted flying insect species, and a second opening in the top of said container, smaller than said first opening and large enough to prevent film closure by a liquid wherein said second opening maintains air pressure in said container, (b) adjusting said wick to provide a uniform emission rate of said at least one attractant for maximum attraction of said target insect over an extended period, and (c) hanging at least one of said trap in a location suspected of being infested by at least one of a targeted pest flying insect;

wherein said container emits attractant for at least about six months without replenishment of said attractant.

* * * * *